United States Patent [19]

Sternby

[11] Patent Number: 5,733,257
[45] Date of Patent: Mar. 31, 1998

[54] METHOD FOR CALIBRATING A PUMP SEGMENT USED IN A PERISTALTIC PUMP AND A MEDICAL MACHINE ADAPTED FOR CARRYING OUT THE METHOD

[75] Inventor: Jan Sternby, Lund, Sweden

[73] Assignee: Gambro AB, Sweden

[21] Appl. No.: 602,749

[22] PCT Filed: Oct. 10, 1994

[86] PCT No.: PCT/SE94/00952

§ 371 Date: Feb. 22, 1996

§ 102(e) Date: Feb. 22, 1996

[87] PCT Pub. No.: WO95/10310

PCT Pub. Date: Apr. 20, 1995

[30] Foreign Application Priority Data

Oct. 11, 1993 [SE] Sweden ............................ 9303319

[51] Int. Cl.[6] .................................................. A61M 1/00
[52] U.S. Cl. ........................................................ 604/27
[58] Field of Search ............................... 604/30–34, 49, 604/65–67, 151, 246; 128/DIG. 13, 12

[56] References Cited

U.S. PATENT DOCUMENTS 4,797,655  1/1989  Orndal et al. ..................... 604/67
5,057,278 10/1991  Maxwell et al. .................. 604/65
5,372,709 12/1994  Hood ................................. 604/65

FOREIGN PATENT DOCUMENTS

A10315312   5/1989  European Pat. Off. .
WOA19006781 6/1990  WIPO .
WOA19109229 6/1991  WIPO .

Primary Examiner—Michael Buiz
Assistant Examiner—Manuel Mendez
Attorney, Agent, or Firm—Lerner, David, Littenberg, Krumholz & Mentlik

[57] ABSTRACT

A method and medical machine for calibrating a peristaltic pump (36, 39) intended to be used in connection with the medical machine, such as a dialysis machine. The machine comprises an internal fluid flow meter (18, 19). Fluid is introduced into the pump segment (36) and is pumped by the peristaltic pump at a substantially constant rotation rate. Three different inlet pressures are obtained and measured by a pressure meter (16) and the corresponding fluid flow is measured by the internal fluid flow meter (18, 19) for obtaining calibration pair values. A calibration curve is calculated from said pair values by a computer (23) inside the medical machine. The actual fluid flow rate is determined by said computer (23) from said calibration curve based on the actual inlet pressure and the actual revolution rate of the propelling means.

23 Claims, 7 Drawing Sheets

METHOD FOR CALIBRATING A PUMP SEGMENT USED IN A PERISTALTIC PUMP AND A MEDICAL MACHINE ADAPTED FOR CARRYING OUT THE METHOD

FIELD OF INVENTION

The present invention relates to a method for calibrating a pump segment used in a peristaltic pump and a device adapted for carrying out the method.

The invention is intended to be used within the medical field and particularly in connection with hemodialysis, hemodiafiltration and hemofiltration. It is however clear for the skilled person that the invention has many other fields of application, e.g. dialysis in general.

PRIOR ART

It is well known that the flow rate obtained from a peristaltic pump depends on many factors such as pump speed, elasticity and diameter of the pump segment and the pressure upstreams and downstreams of the pump.

When such a peristaltic pump is used in connection with a dialysis machine, such as GAMBRO AK100, including a peristaltic pump, the flow through the peristaltic pump is calculated as being proportional to the revolution rate of the pump. To obtain the flow rate, the revolution rate is multiplied by a calibration factor which is dependent on inter alia the inner diameter of the pump segment used. This can lead to substantial errors in the fluid flow as presented on a display of the dialysis machine. This is especially true at larger flows, where the pressure upstreams of the pump can be very low.

The above mentioned dialysis machine, GAMBRO AK 100, includes an option to include a pressure meter just upstreams of the peristaltic pump instead of a pressure monitoring arrangement which otherwise is standard.

GAMBRO AK 100 machine is further provided with a safety coupling, to which the dialysis fluid tubes are connected during cleaning of the dialysis fluid circuit in the monitor. As will appear below, such a safety coupling can advantageously be used when carrying out the present invention. Examples of such safety couplings are described in U.S. Pat. Nos. 4,122,010 and 4,728,496. Moreover, U.S. Pat. No. 4,762,618 describes further components which can be included in the device according to the present invention.

WO 91/09229 discloses a peristaltic pump, in which the pumping action is adjusted in dependence of the outer diameter of the tubing after a certain time period. The motor speed is adjusted for maintaining an approximately constant flow rate of infusion.

A peristaltic pump of the dialysis machine GAMBRO AK 100 is provided with a pump segment included in a set of tubings, which is exchanged at each treatment. During one treatment, a patient is connected to the set of tubings by a fistula needle. The blood of the patient is taken out into an extracorporeal circuit and passes the pump segment of the peristaltic pump.

Such set of tubings are made of inexpensive PVC-material. Thus, the diameter of the pump segment can vary considerably, due to manufacturing tolerances. Moreover, a pump segment having the same outer diameter can have different inner diameter, due to different wall thickness. Still further, a pump segment having the same internal diameter can have different flow resistance, due to different inner surface roughness or other dimension alterations.

In order to take account for pump segments having different properties, it is necessary to calibrate the peristaltic pump for each new pump segment used. This will mean that the peristaltic pump will need to be recalibrated for each treatment.

Before each treatment, the set of tubings and the dialyzer are primed with a sterile priming solution. Moreover, the part of the dialyzer being connected to the dialysis solution is primed with ordinary dialysis solution and a transmembrane pressure is supplied for testing the dialyzer.

DISCLOSE OF THE INVENTION

According to the present invention there is provided a method of calibrating a peristaltic pump intended to be used in connection with a medical machine comprising an internal fluid flow meter. The peristaltic pump includes a replaceable pump segment and propelling means for advancing a fluid or liquid inside the pump segment. According to the invention, the method comprises introducing a fluid to said pump segment, when placed in position in said propelling means; pumping said fluid by said peristaltic pump at a constant revolution rate of said propelling means; obtaining and measuring at least one adjusted inlet pressure to said pump segment; and measuring the fluid flow rate through said pump segment during said adjusted inlet pressure by said internal fluid flow meter of the medical machine, for obtaining at least one calibration pair values. Preferably, at least three calibration pair values are obtained and a calibration curve is calculated from said calibration pair value or values for the relationship between the fluid flow rate and inlet pressure at said constant revolution rate, whereupon the actual fluid flow rate is obtained from said calibration curve based on the actual inlet pressure and the actual revolution rate of the propelling means.

According to one embodiment of the invention, the fluid flow from the outlet of the peristaltic pump, during said at least one adjusted inlet pressure, is introduced into the medical machine for obtaining said fluid flow rate from said internal fluid flow meter of the medical machine. An adjustable throttle valve supplies said adjusted inlet pressures.

In another embodiment, the inlet flow to said pump segment is obtained from an outlet of said medical machine, said inlet flow rate being mesured by said internal flow meter of said medical machine. In this case, the adjusted inlet pressures are obtained from an internal pump of said medical machine, said internal pump being operated so as to provide said inlet pressures, or altenatively by an adjustable throttle valve.

Preferably, said medical machine is a dialysis machine comprising at least one internal fluid flow meter.

The flow through a pump segment also changes over time, calculated from the start of treatment. This time is measured and the actual determined fluid flow is compensated for the time. Alternatively, the calibration is performed after the laps of a certain time, for example after more than 15 minutes, preferably after more than 30 minutes.

The invention also relates to a medical machine for carrying out the method.

DETAILED DESCRIPTION OF THE DRAWINGS

Figure 1:
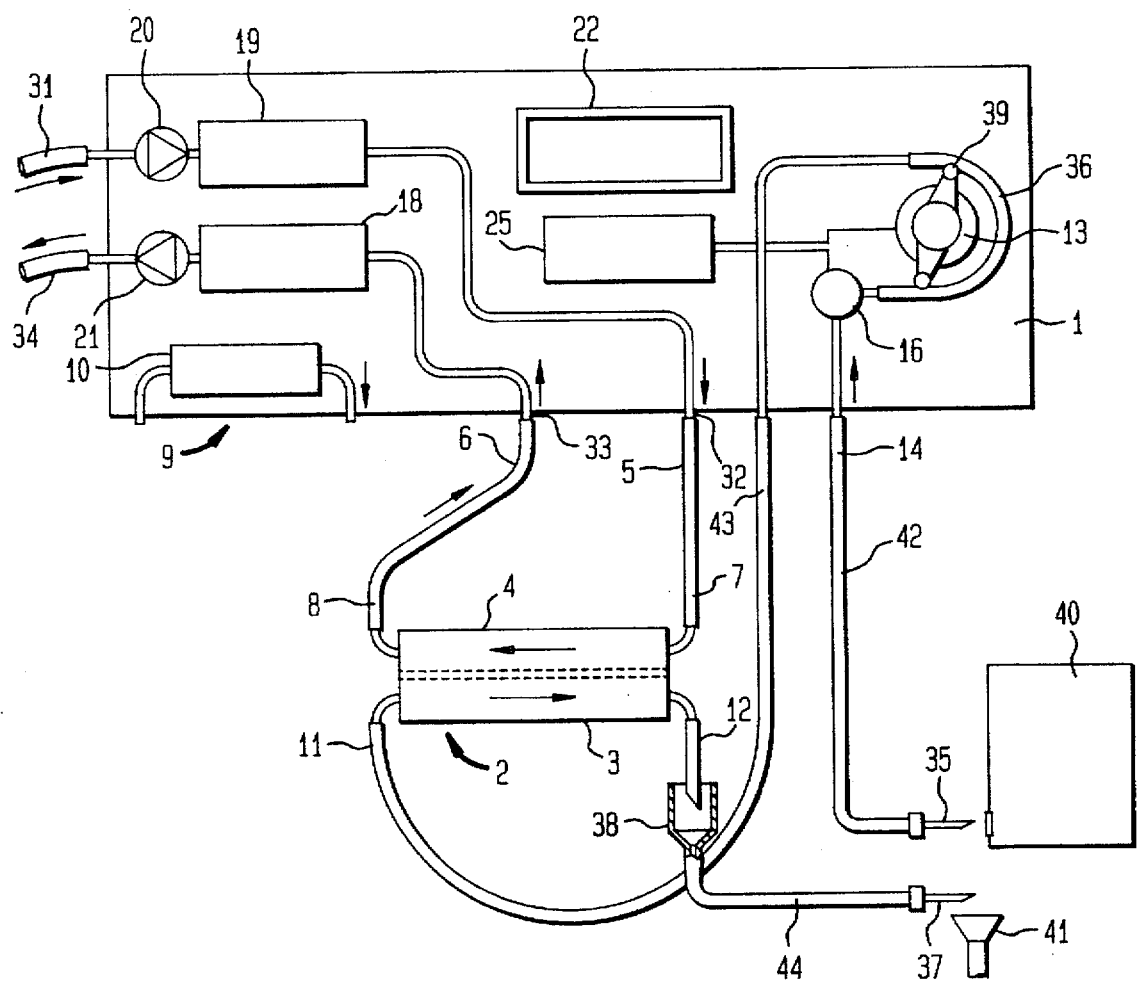
FIG. 1 is a schematic view of a dialysis machine adapted for priming.

FIG. 1 is a schematic diagram of a dialysis machine provided with a set of tubings and a dialyzer as set up before the start of a treatment for priming purpose.

The dialysing machine can be GAMBRO AK 100 intended for hemodialysis. Only those parts and details which are necessary for understanding the present invention are shown in FIG. 1.

The dialysis machine 1 comprises an inlet 31 for dialysis solution leading to an inlet pump 20. Then, the dialysis solution passes through a flow meter 19 for measuring the fluid flow rate. From the flow meter 19, the dialysis solution is emitted through a dialysate outlet 32.

From dialysate outlet 32, the dialysis solution is passed through a dialyzer 2, as explained in more details below, and back to a return inlet 33. From the return inlet 33, the dialysis solution passes through a second flow meter 18 and a pump 21 to a waste outlet 34. The spent dialysis solution is given off through waste outlet 34 to a waste.

The dialyzer 2 comprises two compartments, a first of which 3 is intended to comprise blood, and a second of which 4 is intended to comprise a dialysis solution. The second compartment 4 has one inlet 7 and one outlet 8, which are connected to dialysate outlet 32 and return inlet 33 via hoses 5 and 6. The first compartment 3 has one inlet 11 and one outlet 12. Inlet 11 and outlet 12 are connected to a patient via a set of tubings 14 ended by needles 35 and 37.

The set of tubings comprises a first hose 42 connecting needle 35 to the inlet of a peristaltic pump segment 36, the oulet of which being connected to the inlet 11 of dialyzer 2 via a second hose 43. The outlet 12 of dialyzer 2 is connected to a drip chamber 38 and further to needle 37 via a third hose 44. The drip chamber 38 is intended for ensuring that no air is delivered to the patient.

Before using the dialysis machine provided with the set of tubings and dialyzer, it is necessary to prime the parts. The priming takes place in the following way.

The blood inlet needle 35 is connected to a container 40 comprising sterile priming solution. The priming solution is pumped via needle 35, blood tubing hose 42, pump segment 36, hose 43, inlet 11, dialyzer first compartment 3, outlet 12, drip chamber 38 and patient needle 37 to a waste 41. At the same time, dialysis solution is delivered to the second compartment 4 of the dialyzer 2 via solution inlet 31, pump 20, flow meter 19, outlet 32, hose 5, inlet 7, second compartment 4 of dialyzer, outlet 8, hose 6, inlet 33, flow meter 18, pump 21, waste outlet 34 to a waste. Usually pumps 20 and 21 are operated so that a low or negative pressure prevails in the second compartment 4 creating a transmembrane pressure over the membrane between the first compartment 3 and the second compartment 4 of the dialyzer 2. This transmembrane pressure generates an ultrafiltration flow through the membrane from the first compartment 3 to the second compartment 4. Thus, the outlet flow through outlet 8 of dialyzer 2 is larger than the inlet flow through inlet 7. The difference between those flows are measured by flow meters 18 and 19.

The dialyzer 2 is tilted and moved until all air has escaped from the dialyzer. At the same time, any loose particles within the dialyzer 2 or its connections are removed by the fluid flow.

After priming, needles 35 and 37 are replaced by sterile needles and connected to the patient for taking out the blood of the patient into an extracorporeal circuit through the set of tubings, the peristaltic pump and the dialyzer.

The blood flow rate through the extracorporeal circuit is, according to the prior art, calculated as a calibration factor multiplied by the revolution rate of a rotor 39 of the peristaltic pump 13. The calibration factor is determined on the basis of the internal diameter of the pump segment 36.

The blood flow rate thus obtained will be in error if the inlet pressure to the peristaltic pump is low so that a substantial pressure difference is created over the peristaltic pump. Within the field of peristaltic pumps, it is known to take account of the pressure at the inlet of the pump segment and to adapt the calculated flow rate in dependence of the measured pressure, confer e.g. Danish patent application No. 74-4853 (Sandoz AG). However, due to the manufacturing tolerances of a PVC pump segment, it is necessary to calibrate the pump segment each time a new treatment starts.

According to the present invention, such calibration takes place by using the internal equipment of a dialysis machine (or other medical machine comprising a flow meter).

Figure 2:
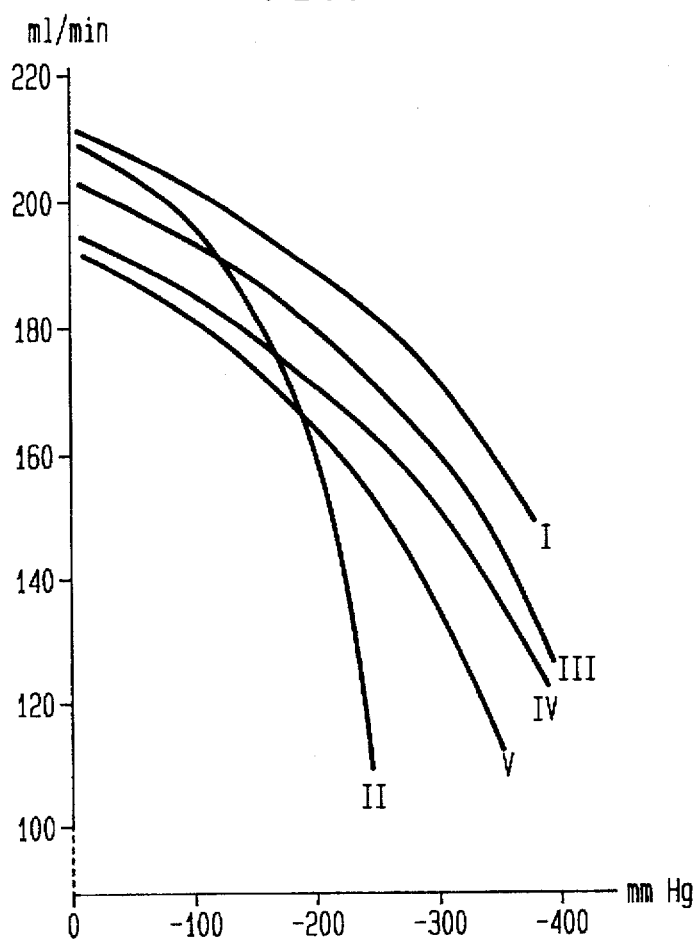
FIG. 2 is a diagram showing calibration curves for pump segments of five different brands.

FIG. 2 shows how the fluid flow, given on the vertical axle, through pump segments of five different brands is heavily dependent on the pressure, given on the horizontal axle, upstreams of the pump at constant pump speed. Despite constant pump speed of 21 revolutions per minute, the flow drops heavily with reducing pressure upstreams of the pump. Large negative pressure upstreams of the pump can occur if for example too narrow a needle is chosen or if the needle and/or blood tubes are blocked in some way between the patient and the pump. One reason for this can be that the negative pressure has a tendency to keep the pump segment pressed together even after the pump roll has passed. This effect is of course reduced if the pump segment has a large wall thickness and an elastic material is used.

Figure 3:
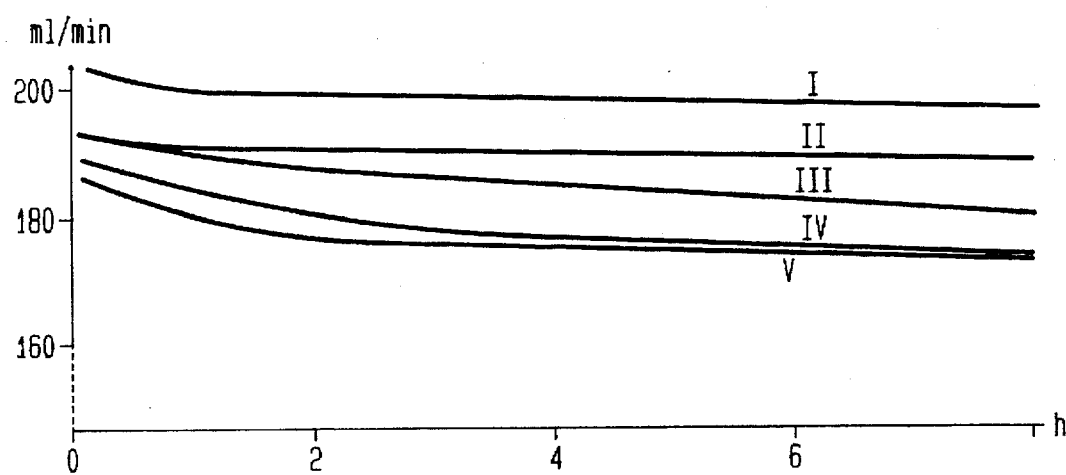
FIG. 3 is a diagram showing the same pump segments dependency on time.

FIG. 3 shows how the fluid flow through one and the same pump segment is dependent on time. This figure also shows how the pump efficiency changes with time for pump segments of five different brands.

Figure 4:
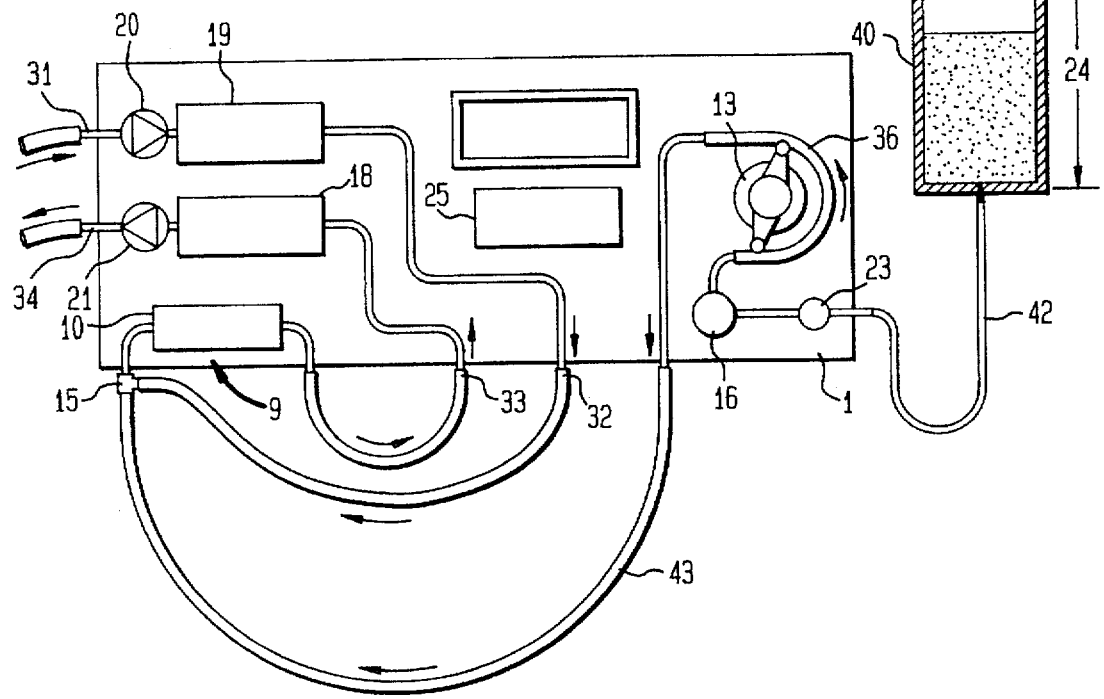
FIG. 4 is a schematic view similar to FIG. 1 and shows a first embodiment of the present invention.

One way of calibrating a peristaltic pump segment using a fluid flow meter internal of the dialysis machine is shown in FIG. 4. In this first embodiment, the dialyzer 2 is disconnected, compared with FIG. 1, and hoses 5 and 6 are connected to a safety by-pass circuit 9, including a pressure monitor 10. The dialysis machine is so adapted, that certain machine operations can only be performed when hoses 5 and 6 are connected to said by-pass circuit 9. Such operations are for example disinfection and cleaning of the machine and includes calibration of the peristaltic pump according to the first embodiment of the present invention.

By-pass circuit 9 includes a second inlet connection 15, which can be placed on the dialysis machine or be a T-connector at hose 6 or hose 5, as shown in FIG. 4. The connector 15 is connected to the outlet of the peristaltic pump segment. The inlet of the peristaltic pump segment is connected to the bag or container 40 comprising sterile priming solution as described in connection with FIG. 1.

Furthermore, the pump segment comprises a connector 16 for connection to a pressure meter positioned internal of the dialysis machine. Thus, the inlet pressure to the peristaltic pump can be measured by the internal pressure meter. The measured pressure is fed to a control and/or monitoring circuit 25, which also includes an inlet for rotor speed of the perstialtic pump.

The dialysis machine is now operated so that a certain dialysate priming flow is passing inlet 31, pump 20, fluid flow meter 19, dialysate outlet 32, by-pass circuit 9, return inlet 33, fluid flow meter 18, pump 21 to waste outlet 34. Pumps 20 and 21 are driven so as to provide a predetermined pressure corresponding to normal outlet pressure for the peristaltic pump during normal operation, for example a positiv pressure of about 200 mm Hg.

The peristaltic pump is operated at a certain constant revolution rate, whereby sterile solution is pumped from container 40, through pump segment 36 to connector 15 and then through fluid flow meter 18 to the waste outlet 34. The dialysis machine measures a fluid flow differential between fluid flow meters 19 and 18, and the differential is the addition from the peristaltic pump. At the same time, the pressure at the inlet of the peristaltic pump segment is measured.

The measured pair of values are stored in the calculating circuit 25, which usually is a computer of the dialysis machine. Then, the inlet pressure is changed and new pairs of measured values of the fluid flow and the inlet pressure is stored. The procedure is repeated until sufficient number of pairs of measured values are obtained. The computer calculates a calibration curve, which then is used for determining the actual fluid flow during subsequent operation of the dialysis machine.

The different inlet pressures can be obtained in different ways. Thus, it is possible to alter the height position of the container 40, thereby to obtain different inlet pressures as suggested by arrow 24. Usually, it is desired to have negative pressures, and it is not possible to lower the container 40 too much. In order to have a more convenient adjustment of the inlet pressure, an adjustable throttle valve 23 is used as shown in FIG. 4. Preferably, the throttle valve is positioned at the medical machine and is controlled by said machine. Alternatively, it is possible to place the throttle valve at the inlet hose 42, whereby the valve can be adjusted manually or automatically.

The method according to the first embodiment can be used in connection with initial filling up of the dialysis machine, when no dialyzer is connected.

Figure 5:
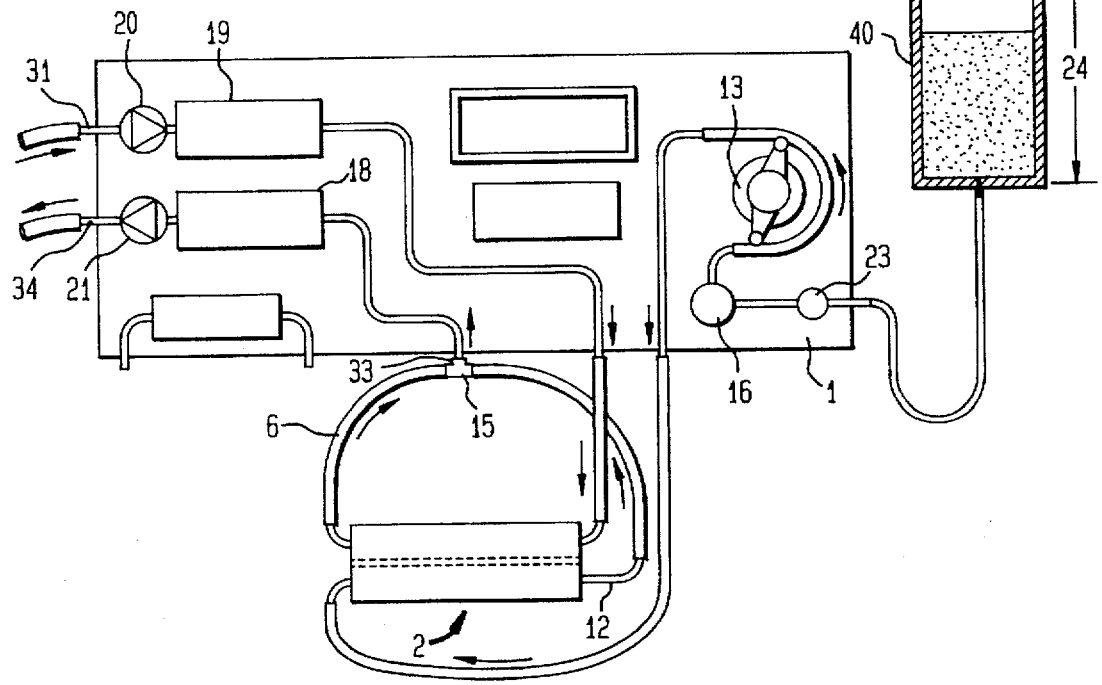
FIG. 5 is a schematic view similar to FIG. 4 and shows a second embodiment of the invention.

In a second embodiment shown in FIG. 5, the calibration is performed during priming of the dialyzer as shown and described in connection with FIG. 1. However, the outlet from the dialyzer 12 is not fed to a waste 41 but connected to an inlet connector 15' of the dialysis machine adjacent return inlet 33. The connector 15' is shown in FIG. 5 as a T-connector of hose 6.

The operation of the second embodiment is the same as for the first embodiment, but has the advantage that the dialyzer 2 is ready for use after the priming combined with calibration of the peristaltic pump.

Figure 6:
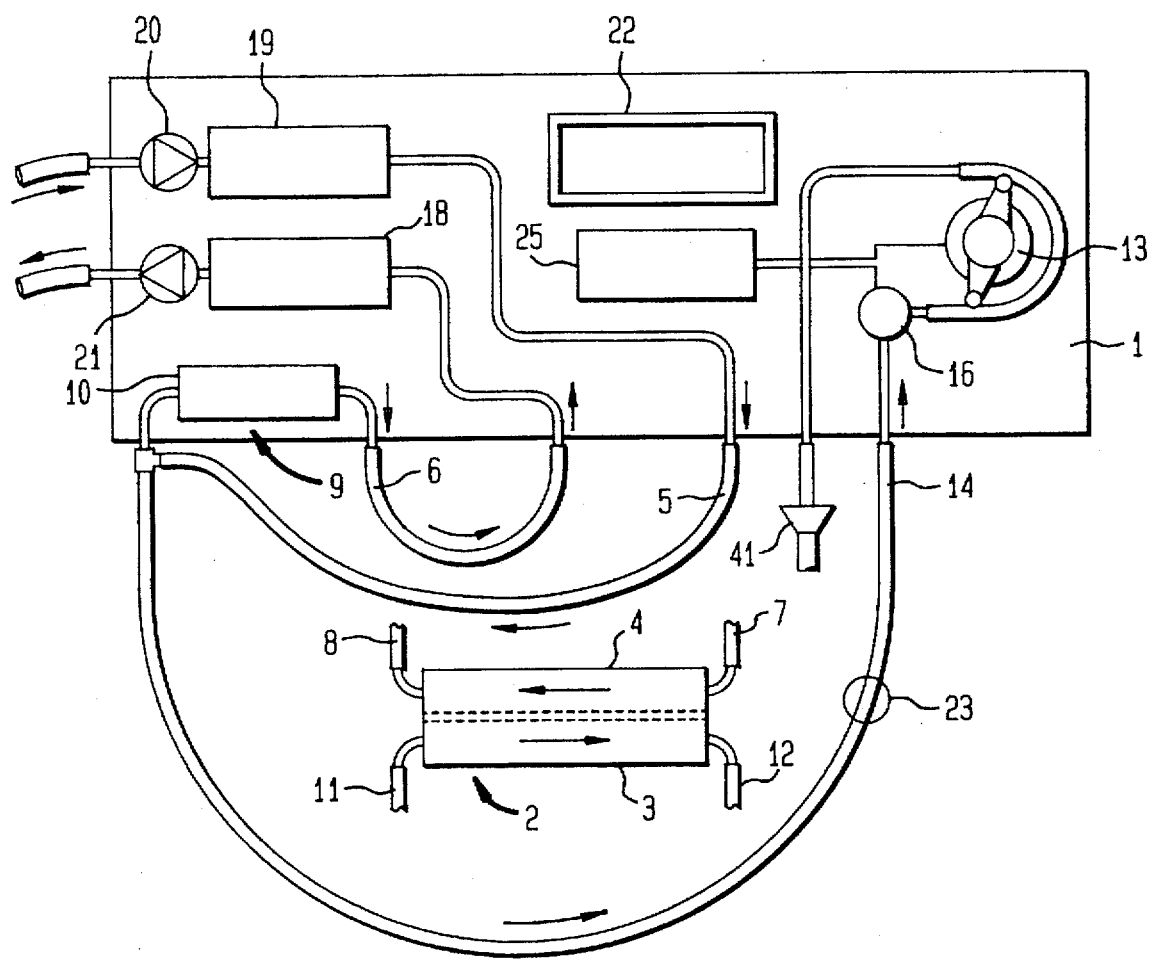
FIG. 6 is a schematic view similar to FIGS. 4 and shows a third embodiment of the invention.

It is also possible to use the dialysis solution from the dialysis machine for calibrating the peristaltic pump. A third embodiment of the invention is shown in FIG. 6. This embodiment is similar to the embodiment according to FIG. 4, but the inlet to the peristaltic pump is connected to the T-connector 15. The outlet from the peristaltic pump is connected to a waste 41.

In this third embodiment, the pumps 20 and 21 of the dialysis machine are driven so as to provide a certain negative pressure at the by-pass circuit 9 where the inlet to the peristaltic pump is connected. The peristaltic pump is started and takes out a fluid flow from the dialysate flow. Thus, fluid flow meter 18 shows a lower fluid flow rate than fluid flow meter 19 and the difference is the fluid flow to the peristaltic pump. The pressure between pumps 20 and 21 is equal to the inlet pressure to the peristaltic pump. Thus, the computer of the dialysis machine is provided with pair of values of fluid flow rate and inlet pressures for obtaining a calibration curve.

In this embodiment, it is possible to adjust the inlet pressure continuously from a small positive pressure to a substantial negative pressure for obtaining the entire calibration curve. The calibration procedure can be repeated for several revolution rates for the peristaltic pump rotor to have several sets of calibration curves.

Alternatively, the negative pressure can be obtained with and adjusted by means of an adjustable throttle valve 23 as mentioned above.

Figure 7:
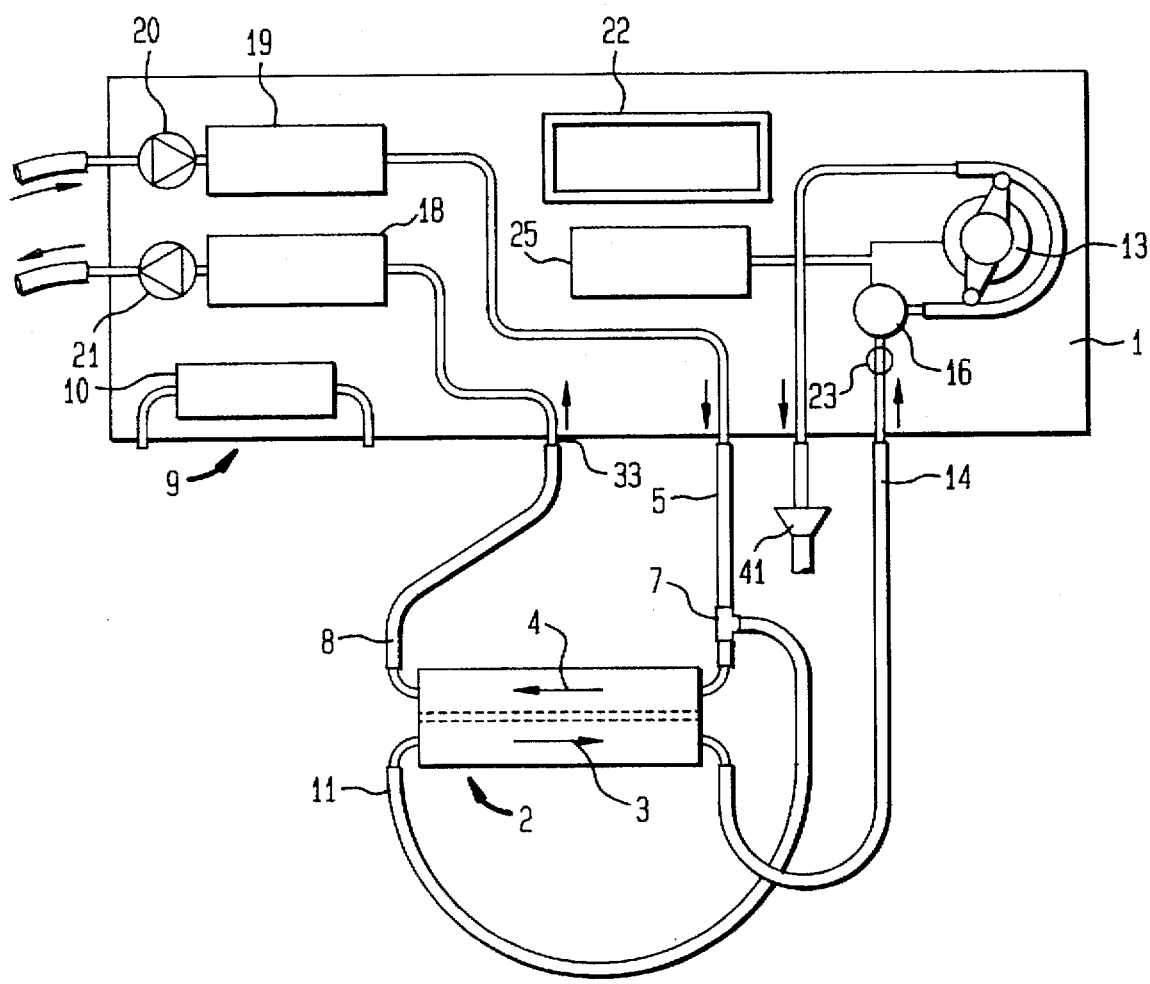
FIG. 7 is a schematic view similar to FIG. 4 and shows a fourth embodiment of the invention

FIG. 7 shows a fourth embodiment of the invention where the calibration takes place during the priming of the dialyzer as in FIG. 5, but using the method of FIG. 6.

It might be impossible to use the dialysate for calibrating the peristaltic pump segment if it cannot be assured that the dialysate is completely sterile, since the pump segment subsequently will be used for passing blood in an extracorporeal circuit, which must be sterile.

However, certain dialysis machines have an outlet for sterile filtered solution used for infusion during hemofiltration or hemodiafiltration, either post- or preinfusion. Such a dialysis machine is for example GAMBRO AK100 ULTRA.

Figure 8:
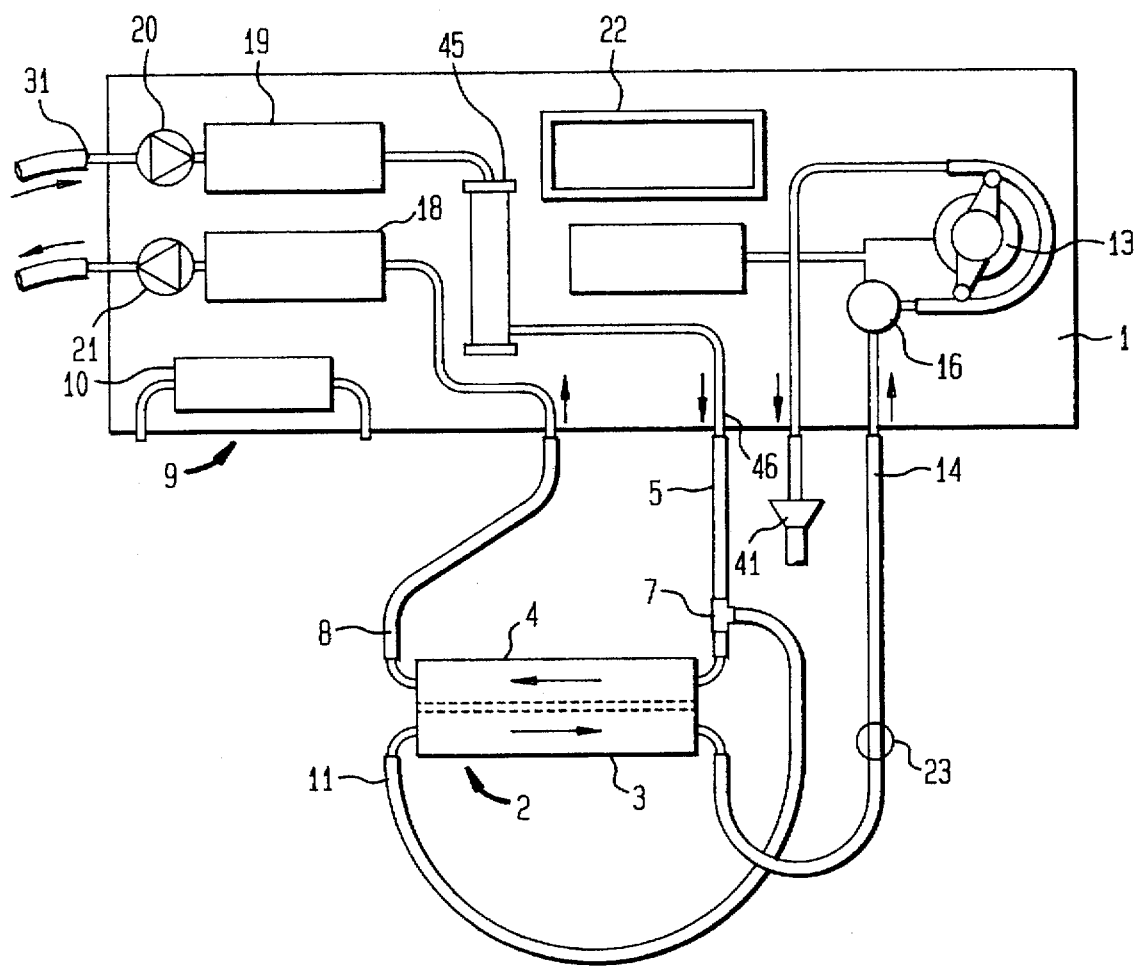
FIG. 8 is a schematic view similar to FIG. 7 and shows a fifth embodiment of the invention.

According to a fifth emodiment of the invention shown in FIG. 8, the dialysis solution used for priming and calibration is first passed through a sterile filter. The dialysis solution through inlet 31 is passed via pump 20 and fluid flow meter 19 to a sterile filter 45, which can be a hollow fibre filter or any other filter having a membran capable of passing solutes having a low molecular weight while preventing bacteria and endotoxins from passing the membrane.

The filtered dialysis solution is emitted through a sterile solution outlet 46 and usually added to an infusion inlet of the drip chamber. A preinfusion is performed by adding the sterile filtered dialysis solution adjacent inlet 11.

The fifth embodiment of the present invention includes using the sterile filtered solution for priming the dialyzer 2 and calibrating the peristaltic pump segment. This fifth embodiment is shown in FIG. 8 and corresponds in all essentials to the fourth embodiment shown in FIG. 7, but the sterile filter 45 has been added. The operation is obvious from the above description.

Figure 9:
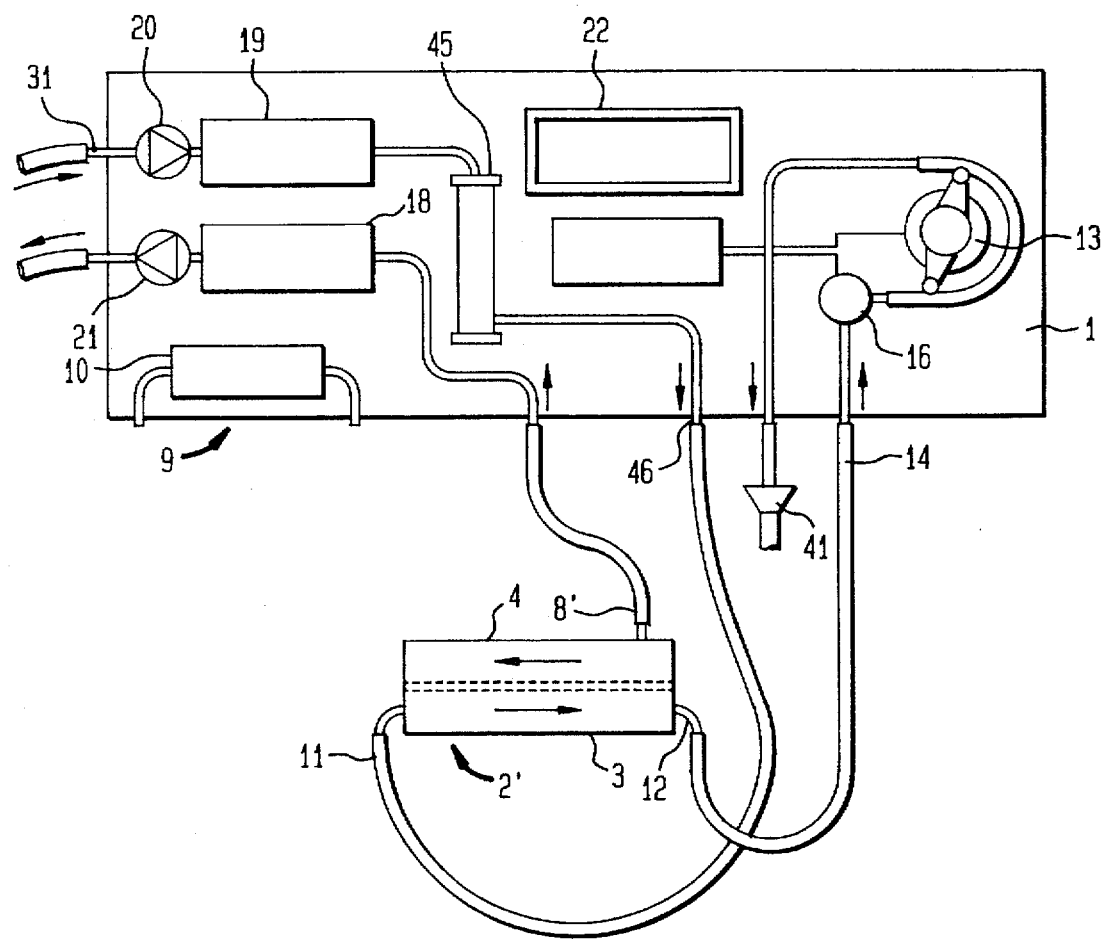
FIG. 9 is a schematic view similar to FIG. 8 and shows a sixth embodiment of the invention.

A sixth embodiment of the invention is shown in FIG. 9 and comprises a dialyzer 2' used for hemofiltration, a so called hemofilter. Such a hemofilter lacks inlet 7 for dialysis solution and an ultrafiltrate is taken out from the blood through outlet 8'. The ultrafiltrate is compensated by addition of substitution solution from sterile filtered outlet 46 as mentioned above. Said hemofilter is primed by dialysis solution from sterile filtered outlet 46. According to the sixth embodiment, the outlet 12 from the hemofilter 2' is fed to the inlet of the peristaltic pump. Thus, the difference between flow meters 19 and 18 is the flow through the peristaltic pump. By means of pumps 20, the inlet pressure to the pump segment can be adjusted. Pump 21 controls the transmembrane pressure. Alternatively, the throttle valve 23 can adjust the inlet pressure. The further operation is obvious from the above given description.

During some types of dialysis, such as single needle dialysis and for infusion of substitution solution during hemofiltration, a second peristaltic pump is used for such purposes. Such second pump can be calibrated in the same way as described above.

It is noted that the peristaltic pump segment is calibrated according to the invention while using a priming solution comprised in a container 40 or a dialysis solution from the dialysis machine. It is noted that blood usually is much more viscous than such solutions. However, the calibration curve is essentially independent of which fluid is pumped as soon as it is non-compressible, since the variation due to different inlet pressures mainly is dependent on the fact that the pump segment is not returned to its circular shape after each pump stroke. Thus, the calibration curve is mainly a property of the material and dimensions of the pump segment proper.

It is noted that the calibration curve will change with time as shown and described with reference to FIG. 3. Such dependency is believed to be mainly dependent on fatigue in the material. It is also known that the elasticity of most plastic materials is very dependent on the temperature. Thus, it is prefered to perform the calibration at a temperature close to 37 degrees Celsius.

Such a temperature is easily achieved in the embodiments according to FIGS. 6, 7 and 8. In the embodiments according to FIGS. 4 and 5, such temperature can be obtained by heating the priming solution in container 40.

In order to obtain a calibration curve, the calibration pair values are compared to known calibration curves stored in the medical machine and the most correct calibration curve is selected. To select a correct curve, it is sufficient to have two pairs of values. One of the pair values can be given by the manufacturer for the actual type of pump segment, although measured values are preferred.

Generally, the calibration curve is a second degree curve and it can be approximated by using three different pair values (of which one can be given by the manufacturer).

It is possible to take several measured pair values for the same input pressure and calculate the mean value thereof for increasing the probability of having the correct calibration curve. Finally, as described in connection with FIG. 6, it is possible to obtain the entire calibration curve or set of calibration curves by continuously adjusting the inlet pressure and measure the corresponding fluid flow. Further alternatives are obvious to a skilled person.

Account is also taken for the dependency of the fluid flow by time. Such adjustment is less dependent on different properties of the actual pump segment used but is more constant for the actual brand of pumps segment and is furthermore rather small, such as less than about 5%. Thus, values obtained from a data sheet can be used for such compensation.

It is evident from FIG. 3 that the decrease in fluid flow is obtained after about 60 minutes and for some types even earlier, such as after 30 minutes. By performing the calibration after that the decrease has substantially occured, such as after 15, 30 or 60 minutes, the time dependency can be neglected.

The actual fluid flow through the peristaltic pump during operation of the medical machine, can be obtained by measuring the inlet pressure and revolution rate of the peristaltic pump. From the calibration curves, an actual fluid flow can be determined. Such actual flow can be shown on the medical machine on a display thereof. Alternatively, said actual flow can be fed to a control device adapted to adjust the peristaltic pump to obtain a desired fluid flow. Further possibilities are obvious to a skilled person.

As mentioned above, the invention is particurlarly intended to be used at dialysis. Some dialysis machines, such as GAMBRO AK100, has an internal fluid flow meter directly measuring the fluid flow by using a magnetic field and measuring the electric properties of the fluid flow under influence of said magnetic field. Other dialysis machines have other types of fluid flow meters using other physical properties for measuring the fluid flow. Still further dialysis machines have constant deplacement pumps for measuring the fluid flow and simultaneous pumping the fluid, i.e. generating a pressure. All such types of "flow meters" are intended to be within the definition of the claims.

The invention is of course not limited to the embodiments described above, but can be varied within the scope of the appended patent claims. Different combinations of features and properties from the described embodiments can be used. It should hereby be observed that a dialysis machine ordinarily contains a large number of components apart from those shown schematically in the figures. Additionally account can also be taken of further operative factors apart from those mentioned above. For example the height difference between the pressure meter 16 and the safety coupling 9 can also be taken into account.

I claim:

1. A method for calibrating a peristaltic pump including a replaceable tube segment having an inlet and an outlet and propelling means for propelling a fluid through said replaceable tube segment, said method comprising introducing a fluid into said inlet of said replaceable tube segment, pumping said fluid through said replaceable tube segment by operating said propelling means at a substantially constant propelling rate, measuring at least one adjusted inlet pressure for said fluid at said inlet to said replaceable tube segment, and measuring the fluid flow rate through said replaceable tube segment corresponding to said at least one adjusted inlet pressure in order to thereby obtain at least one calibration pair value for said peristaltic pump.

2. The method of claim 1 wherein said peristaltic pump is adapted for use with medical treatment apparatus including an internal fluid flow meter, and wherein said measuring of said fluid flow rate is carried out utilizing said internal fluid flow meter.

3. The method of claim 2 wherein said measuring of said fluid flow rate comprises flowing said fluid from said outlet of said replaceable tube segment to said internal fluid flow meter of said medical treatment apparatus.

4. The method of claim 3 including providing said adjusted inlet pressure by adjustably throttling said fluid flow to said inlet of said replaceable tube segment.

5. The method of claim 2 wherein said medical treatment apparatus includes at least one fluid outlet, and including measuring said fluid flow rate by passing a fluid from said at least one fluid outlet to said inlet of said replaceable tube segment and measuring said fluid flow rate utilizing said internal fluid flow meter of said medical treatment apparatus.

6. The method of claim 5 wherein said medical treatment apparatus includes at least one internal pump, and including supplying said fluid to said inlet of said replaceable tube segment by means of said at least one internal pump.

7. The method of claim 2 wherein said medical treatment apparatus comprises a dialysis machine.

8. The method of claim 1 wherein said measuring of said fluid flow rate comprises measuring at least two of said fluid flow rates through said replaceable tube segment corresponding to at least two of said adjusted inlet pressures in order to obtain at least two calibration pair values for said peristaltic pump, and calculating a calibration curve for said calibration pair values representing the relationship between said fluid flow rate and said inlet pressure at said substantially constant propelling rate.

9. The method of claim 8 including obtaining at least a third calibration pair value for said peristaltic pump comprising a standard pair value corresponding to said peristaltic pump.

10. The method of claim 8 including selecting an actual inlet pressure and an actual constant propelling rate and determining the actual fluid flow rate from said calibration curve for said selected actual inlet pressure and said selected actual constant propelling rate.

11. The method of claim 1 including adjusting said at least one calibration pair value by compensating for the time dependency of said fluid flow rate.

12. The method of claim 11 including compensating for said time dependency by means of a standard value compensation for said peristaltic pump.

13. The method of claim 11 including compensating for said time dependency by permitting a predetermined time period to elapse for said pumping of said fluid through said replaceable tube segment before calibrating said peristaltic pump.

14. The method of claim 13 wherein said predetermined time period comprises at least about 15 minutes.

15. The method of claim 13 wherein said predetermined time period comprises at least about 30 minutes.

16. A medical treatment apparatus including an internal fluid flow meter and a peristaltic pump comprising a replaceable tube segment including an inlet and an outlet and propelling means for propelling a fluid through said replaceable tube segment at a substantially constant propelling rate, said apparatus including peristaltic pulp calibration means comprising a first hose for connecting a source of a solution to said inlet of said replaceable tube segment, a second hose for connecting said outlet of said replaceable tube segment to disposal means, providing means for providing said fluid to said inlet of said replaceable tube segment, pressure measuring means for measuring an adjusted inlet pressure for said fluid at said inlet to said replaceable tube segment, flow measuring means for measuring the fluid flow rate of said fluid through said replacement tube segment during maintenance of said adjusted inlet pressure in order to thereby obtain at least one calibration pair value for said peristaltic pump, and calculation means for calculating a calibration curve from said at least one calibration pair value representing the relationship between said fluid flow rate and said inlet pressure at said substantially constant propelling rate.

17. The apparatus of claim 16 wherein said flow measuring means comprises said internal flow meter.

18. The apparatus of claim 17 including at least one fluid inlet member, and wherein said second hose connects said outlet of said replaceable tube segment to said at least one fluid inlet member upstream of said disposal means, whereby said fluid flow rate can be measured by said internal fluid flow meter.

19. The apparatus of claim 17 including at least one fluid outlet member, and wherein said first hose is connected to said at least one fluid outlet member as said source of said solution, whereby said fluid flow rate can be measured by said internal flow meter.

20. The apparatus of claim 19 including pressure adjusting means for adjusting the pressure at said at least one fluid outlet member thereby adjusting the pressure of said inlet to said adjustable pump segment.

21. The apparatus of claim 16, including determining means for determining the actual fluid flow rate for an actual inlet pressure and an actual constant propelling rate utilizing said calibration curve.

22. The apparatus of claim 16 including an adjustable throttle valve associated with said inlet of said adjustable pump segment for adjusting the inlet pressure of said adjustable pump segment to said adjusted inlet pressure.

23. The apparatus of claim 16 wherein said medical treatment apparatus comprises a dialysis machine.

* * * * *

UNITED STATES PATENT AND TRADEMARK OFFICE
CERTIFICATE OF CORRECTION

PATENT NO. : 5,733,257

DATED : March 31, 1998

INVENTOR(S) : Jan Sternby

It is certified that error appears in the above-identified patent and that said Letters Patent is hereby corrected as shown below:

```
The title page should be deleted to appear as per attached title page.

Columns 1-10 should be deleted and substituted.

Columns 1-12 as per attached.
```

Signed and Sealed this

Sixteenth Day of February, 1999

Attest:

*Attesting Officer*

*Acting Commissioner of Patents and Trademarks*

United States Patent
Sternby

[11] Patent Number: 5,733,257
[45] Date of Patent: Mar. 31, 1998

[54] METHOD FOR CALIBRATING A PUMP SEGMENT USED IN A PERISTALTIC PUMP AND A MEDICAL MACHINE ADAPTED FOR CARRYING OUT THE METHOD

[75] Inventor: Jan Sternby, Lund, Sweden

[73] Assignee: Gambro AB, Sweden

[21] Appl. No.: 602,749
[22] PCT Filed: Oct. 10, 1994
[86] PCT No.: PCT/SE94/00952
  § 371 Date: Feb. 22, 1996
  § 102(e) Date: Feb. 22, 1996
[87] PCT Pub. No.: WO95/10310
  PCT Pub. Date: Apr. 20, 1995

[30] Foreign Application Priority Data

Oct. 11, 1993 [SE] Sweden ............... 9303319

[51] Int. Cl.⁶ ........................ A61M 1/00
[52] U.S. Cl. ........................ 604/27
[58] Field of Search ............ 604/30–34, 49, 604/65–67, 151, 246; 128/DIG. 13, 12

[56] References Cited

U.S. PATENT DOCUMENTS 4,797,655  1/1989  Omdal et al. ............... 604/67
5,057,278  10/1991 Maxwell et al. ............ 604/65
5,372,709  12/1994 Hood ........................ 604/65

FOREIGN PATENT DOCUMENTS

A10315312   5/1989  European Pat. Off.
WOA19006781 6/1990  WIPO.
WOA19109229 6/1991  WIPO.

Primary Examiner—Michael Buiz
Assistant Examiner—Manuel Mendez
Attorney, Agent, or Firm—Lerner, David, Littenberg, Krumholz & Mentlik

[57] ABSTRACT

Methods for calibrating peristaltic pumps are disclosed, including introducing a fluid into the inlet of the replaceable tube segment of the pump, pumping the fluid through the replaceable tube segment at a substantially constant rate, measuring at least one adjusted inlet pressure for the fluid at the inlet to the replaceable tube segment, and measuring the fluid flow rate through the replaceable tube segment corresponding to that at least one adjusted inlet pressure in order to obtain at least one calibration pair value for the peristaltic pump. Apparatus are also disclosed including a medical treatment apparatus such as a dialysis machine including an internal flow meter for measuring the fluid flow rate of the fluid through the replaceable tube segment of the peristaltic pump.

23 Claims, 7 Drawing Sheets

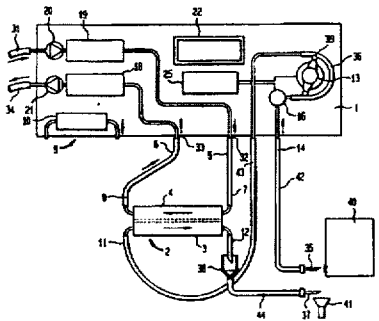

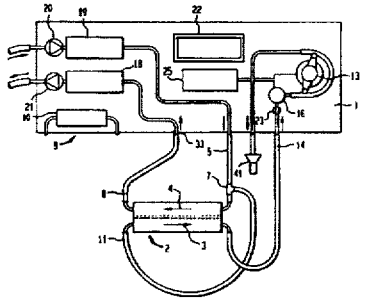

5,733,257

METHOD FOR CALIBRATING A PUMP SEGMENT USED IN A PERISTALTIC PUMP AND A MEDICAL MACHINE ADAPTED FOR CARRYING OUT THE METHOD

FIELD OF THE INVENTION

The present invention relates to a method for calibrating a pump segment used in a peristaltic pump. More particularly, the present invention also relates to a device adapted for carrying out this method.

BACKGROUND OF THE INVENTION

The present invention is intended to be used within the medical field and particularly in connection with hemodialysis, hemodiafiltration and hemofiltration. It will be clear, however, to persons skilled in this art that the invention has many other fields of application, e.g. dialysis in general.

It is well known that the flow rate obtained from a peristaltic pump depends on many factors, such as the pump speed, the elasticity and diameter of the pump segment, and the pressures upstream and downstream of the pump.

When such a peristaltic pump is used in connection with a dialysis machine, such as GAMBRO AK100, which includes a peristaltic pump, the flow through the peristaltic pump is calculated as being proportional to the revolution rate of the pump. To obtain the flow rate, the revolution rate is thus multiplied by a calibration factor which is dependent on, inter alia, the inner diameter of the pump segment being used. This can lead to substantial errors in the fluid flow as it is presented on a display on the dialysis machine. This is especially true at large flow rates where the pressure upstream of the pump can be very low.

The above-mentioned dialysis machine, GAMBRO AK100, includes an option to include a pressure meter immediately upstream of the peristaltic pump instead of a pressure monitoring arrangement, which is otherwise standard.

The GAMBRO AK100 machine is further provided with a safety coupling, to which the dialysis fluid tubes are connected during cleaning of the dialysis fluid circuit in the monitor. As will appear below, such a safety coupling can advantageously be used when carrying out the present invention. Examples of such safety couplings are descried in U.S. Pat. Nos. 4,122,010 and 4,728,496. Moreover, U.S. Pat. No. 4,762,618 describes further components which can be included in the device according to the present invention.

WO 91/09229 discloses a peristaltic pump, in which the pumping action is adjusted dependent upon the outer diameter of the tubing after a certain time period. The motor speed is adjusted for maintaining an approximately constant infusion flow rate.

A peristaltic pump in the dialysis machine GAMBRO AK100 is provided with a pump segment which is included in a set of tubings, which are exchanged for each treatment. During one treatment, a patient is connected to the set of tubings by a fistula needle. The patient's blood is taken out into an extracorporeal circuit, and passes through the pump segment of the peristaltic pump.

Such a set of tubings are generally made of inexpensive PVC-material. Thus, the diameter of the pump segment can vary considerably, primarily due to manufacturing tolerances. Moreover, a pump segment having the same outer diameter can have different inner diameters, due to different wall thicknesses. Still further, a pump segment having the same internal diameter can have different flow resistances, due to different inner surface roughness or other dimensional alterations.

In order to take into account pump segments having different properties, it is necessary to calibrate the peristaltic pump for each new pump segment utilized. This therefore means that the peristaltic pump will need to be recalibrated before each treatment.

Before each treatment, the set of tubings and the dialyzer are primed with a sterile priming solution. Moreover, the part of the dialyzer being connected to the dialysis solution is primed with ordinary dialysis solution, and a transmembrane pressure is supplied for testing the dialyzer.

SUMMARY OF THE INVENTION

In accordance with the present invention, applicant has invented a method for calibrating a peristaltic pump including a replaceable tube segment having an inlet and an outlet and propelling means for propelling a fluid through the replaceable tube segment, the method including introducing a fluid into the inlet of the replaceable tube segment, pumping the fluid through the replaceable tube segment by operating the propelling means at a substantially constant propelling rate, measuring at least one adjusted inlet pressure for the fluid at the inlet to the replaceable tube segment, and measuring the fluid flow rate through the replaceable tube segment corresponding to the at least one adjusted inlet pressure in order to thereby obtain at least one calibration pair value for the peristaltic pump. Preferably, the peristaltic pump is adapted for use with medical treatment apparatus including an internal fluid flow meter, and measuring of the fluid flow rate is carried out utilizing the internal fluid flow meter.

In accordance with one embodiment of the method of the present invention, measuring of the fluid flow rate comprises measuring at least a pair of the fluid flow rates through the replaceable tube segment corresponding to at least a pair of the adjusted inlet pressures in order to obtain at least two calibration pair values for the peristaltic pump, and calculating the calibration curve for the calibration pair values representing the relationship between the fluid flow rate and the inlet pressure at the substantially constant propelling rate. Preferably, the method includes obtaining at least a third calibration pair value for the peristaltic pump comprising a standard pair value corresponding to the peristaltic pump.

In accordance with another embodiment of the method of the present invention, the method includes selecting an actual inlet pressure and an actual constant propelling rate and determining the actual fluid flow rate from the calibration curve for the selected actual inlet pressure and the selected actual constant propelling rate.

In accordance with another embodiment of the method of the present invention, the method includes adjusting the at least one calibration pair value by compensating for the time dependency of the fluid flow rate. Preferably, the method includes compensating for the time dependency by means of a standard value compensation for the peristaltic pump.

In another embodiment, however, the method includes compensating for the time dependency by permitting a predetermined time period to elapse for the pumping of the fluid through the replaceable tube segment before calibrating the peristaltic pump. Preferably, the predetermined time period is at least about 15 minutes, and most preferably at least about 30 minutes.

In accordance with another embodiment of the method of the present invention, the method includes measuring the fluid flow rate by flowing the fluid from the outlet of the replaceable tube segment to the internal fluid flow meter of the medical treatment apparatus.

In accordance with another embodiment of the method of the present invention, the medical treatment apparatus includes at least one fluid outlet, and the method includes measuring the fluid flow rate by passing a fluid from the at least one fluid outlet to the inlet of the replaceable tube segment and measuring the fluid flow rate utilizing the internal fluid flow meter of the medical treatment apparatus. In a preferred embodiment, the medical treatment apparatus includes at least one internal pump, and the method includes supplying the fluid to the inlet of the replaceable tube segment by means of the at least one internal pump.

In accordance with another embodiment of the method of the present invention, the method includes providing the adjusted inlet pressure by adjustably throttling the fluid flow to the inlet of the replaceable tube segment.

In accordance with a preferred embodiment of the method of the present invention, the medical treatment apparatus comprises a dialysis machine.

In accordance with the present invention, a medical treatment apparatus has also been invented which includes an internal fluid flow meter and a peristaltic pump comprising a replaceable tube segment including an inlet and an outlet and propelling means for propelling a fluid through the replaceable tube segment at a substantially constant propelling rate, the apparatus including peristaltic pump calibration means comprising a first hose for connecting a source of a solution to the inlet of the replaceable tube segment, a second hose for connecting the outlet of the replaceable tube segment to the disposal means, providing means for providing the fluid to the inlet of the replaceable tube segment, pressure measuring means for measuring an adjusted inlet pressure for the fluid at the inlet to the replaceable tube segment, and flow measuring means for measuring the fluid flow rate of the fluid through the replaceable tube segment during maintenance of the adjusted inlet pressure in order to thereby obtain at least one calibration pair value for the peristaltic pump. In one embodiment, the flow measuring means comprises the internal flow meter. In a preferred embodiment, the apparatus includes calculation means for calculating a calibration curve from the at least one calibration pair value representing the relationship between the fluid flow rate and the inlet pressure at the substantially constant propelling rate, and determining means for determining the actual fluid flow rate for an actual inlet pressure and an actual constant propelling rate utilizing the calibration curve.

In accordance with another embodiment of the apparatus of the present invention, the apparatus includes at least one fluid inlet member, and the second hose connects the outlet of the replaceable tube segment to the at least one fluid inlet member upstream of the disposal means, whereby the fluid flow rate can be measured by the internal fluid flow meter.

In accordance with another embodiment of the apparatus of the present invention, the apparatus includes at least one fluid outlet member, and the first hose is connected to the at least one fluid outlet member as the source of the solution, whereby the fluid flow rate can be measured by the internal flow meter.

In accordance with another embodiment of the apparatus of the present invention, the apparatus includes an adjustable throttle valve associated with the inlet of the adjustable pump segment for adjusting the inlet pressure to the adjustable pump segment to the adjusted inlet pressure.

In accordance with another embodiment of the apparatus of the present invention, the apparatus includes pressure adjusting means for adjusting the pressure of the at least one fluid outlet member thereby adjusting the pressure to the inlet to the adjustable pump segment.

In accordance with a preferred embodiment of the apparatus of the present invention, the medical treatment apparatus comprises a dialysis machine.

According to the present invention, a method is provided for calibrating a peristaltic pump intended to be used in connection with a medical machine which includes an internal fluid flow meter. The peristaltic pump includes a replaceable pump segment and propelling means for advancing a fluid or liquid inside the pump segment. According to the invention, the method comprises introducing a fluid to the pump segment, when placed in position in the propelling means; pumping the fluid by means of the peristaltic pump at a constant revolution rate of the propelling means; obtaining and measuring at least one adjusted inlet pressure to the pump segment; and measuring the fluid flow rate through the pump segment during the adjusted inlet pressure by the internal fluid flow meter of the medical machine, for obtaining at least one calibration pair value. Preferably, at least three calibration pair values are obtained, and a calibration curve is calculated from the calibration pair value or values for the relationship between the fluid flow rate and inlet pressure at the constant revolution rate, whereupon the actual fluid flow rate is obtained from the calibration curve based on the actual inlet pressure and the actual revolution rate of the propelling means.

According to one embodiment of the present invention, the fluid flow from the outlet of the peristaltic pump, during maintenance of the at least one adjusted inlet pressure, is introduced into the medical machine for obtaining the fluid flow rate from the internal fluid flow meter of the medical machine. An adjustable throttle valve supplies the adjusted inlet pressures.

In another embodiment, the inlet flow to the pump segment is obtained from an outlet of the medical machine, the inlet flow rate being measured by the internal flow meter of the medical machine. In this case, the adjusted inlet pressures are obtained from an internal pump of the medical machine, the internal pump being operated so as to provide the inlet pressures, or alternatively by an adjustable throttle valve.

Preferably, the medical machine is a dialysis machine comprising at least one internal fluid flow meter.

The flow through a pump segment also changes over time, calculated from the start of treatment. This time is measured, and the actual determined fluid flow is compensated for the time. Alternatively, the calibration is performed after the lapse of a certain time, for example after more than about 15 minutes, preferably after more than about 30 minutes.

The invention also relates to a medical apparatus for carrying out this method.

BRIEF DESCRIPTION OF THE DRAWINGS

The subject matter of the present invention may be for fully appreciated with reference to the following detailed description, which in turn refers to the drawings in which:

FIG. 1 is a schematic representation of a dialysis machine for use in connection with the present invention adapted for priming;

FIG. 2 is a graphical representation showing calibration curves for five different brands of pump segments;

FIG. 3 is a graphical representation showing the time dependency of the five different brands of pump segments referred to in FIG. 2;

FIG. 4 is a schematic representation showing a first embodiment of an apparatus for use in connection with the present invention;

FIG. 5 is a schematic representation of another embodiment of apparatus for use in connection with the present invention;

FIG. 6 is a schematic representation of yet another embodiment of an apparatus for use in connection with the present invention;

FIG. 7 is yet another embodiment of an apparatus for use in connection with the present invention;

FIG. 8 is yet another embodiment of an apparatus for use in connection with the present invention; and FIG. 9 is yet another embodiment of an apparatus for use in connection with the present invention.

DETAILED DESCRIPTION

Referring to the Drawings, in which like reference numerals refer to like elements thereof, FIG. 1 is a schematic diagram of a dialysis machine provided with a set of tubes and a dialyzer as set up for priming purposes before the start of a treatment.

The dialyzing machine can be e.g. of the type of GAMBRO AK100, which is intended for hemodialysis. Only those parts and details which are necessary for understanding the present invention are shown in FIG. 1

The dialysis machine 1 comprises an inlet 31 for dialysis solution leading to an inlet pump 20. Then, the dialysis solution passes through a flow meter 19 for measuring the fluid flow rate. From the fluid flow meter 19, the dialysis solution is emitted through a dialysate outlet 32.

From dialysate outlet 32, the dialysis solution is passed through a dialyzer 2, as explained in more details below, and back to a return inlet 33. From the return inlet 33, the dialysis solution passes through a second flow meter 18 and a pump 21 to a waste outlet 34. The spent dialysis solution is given off through waste outlet 34 as waste.

The dialyzer 2 comprises two compartments, a first of which 3 is intended to comprise blood, and a second of which 4 is intended to comprise a dialysis solution. The second compartment 4 has one inlet 7 and one outlet 8, which are connected to dialysate outlet 32 and return inlet 33 by means of hose 5 and 6. The first compartment 3 has one inlet 11 and one outlet 12. Inlet 11 and outlet 12 are connected to a patient by a set of tubes 14 ended by needles 35 and 37.

The set of tubes comprises a first hose 42 connecting needle 35 to the inlet of a peristaltic pump segment 36, the outlet of which is connected to the inlet 11 of dialyzer 2 be means of a second hose 43. The outlet 12 of dialyzer 2 is connected to a drip chamber 38 and further to needle 37 through a third hose 44. The drip chamber 38 is intended for ensuring that no air is delivered to the patient.

Before using the dialysis machine provided with the set of tubes and dialyzer, it is necessary to prime the apparatus. The priming takes place in the following manner.

The flood inlet needle 35 is connected to a container 40 comprising sterile priming solution. The priming solution is pumped through needle 35, blood tubing hose 42, pump segment 36, hose 43, inlet 11, dialyzer first compartment 3, outlet 12, drip chamber 38 and patient needle 37 to waste 41. At the same time, dialysis solution is delivered to the second compartment 4 of the dialyzer 2 through solution inlet 31, pump 20, flow meter 19, outlet 32, hose 5, inlet 7, second compartment 4 of the dialyzer, outlet 8, hose 6, inlet 33, flow meter 18, pump 21, waste outlet 34 to waste. Usually pumps 20 and 21 are operated so that a low or negative pressure prevails in the second compartment 4 creating a transmembrane pressure over the membrane between the first compartment 3 and the second compartment 4 of the dialyzer 2. This transmembrane pressure generates an ultrafiltration flow through the membrane from the first compartment 3 to the second compartment 4. Thus, the outlet flow through outlet 8 of dialyzer 2 is larger than the inlet flow through inlet 7. The difference between those flows is measured by flow meters 18 and 19.

The dialyzer 2 is tilted and moved until all air has escaped from the dialyzer. At the same time, any loose particles within the dialyzer 2 or its connections are removed by the fluid flow.

After priming, needles 35 and 37 are replaced by sterile needles and connected to the patient for removing the patient's blood into an extracorporeal circuit through a set of tubes, the peristaltic pump and the dialyzer.

The blood flow rate through the extracorporeal circuit is, according to the prior art, calculated as a calibration factor multiplied by the revolution rate of a rotor 39 of the peristaltic pump 13. The calibration factor is determined on the basis of the internal diameter of the pump segment 36.

The blood flow rate thus obtained will be in error if the inlet pressure to the peristaltic pump is low so that a substantial pressure difference is created over the peristaltic pump. Within the field of peristaltic pumps, it is known to take into account the pressure at the inlet of the pump segment and to adapt the calculated flow rate depending upon the measured pressure, see e.g. Danish patent application No. 74-4853 (Sandoz AG). However, due to the manufacturing tolerances of a PVC pump segment, it is necessary to calibrate the pump segment each time a new treatment is initiated.

According to the present invention, such calibration takes place by using the internal equipment of a dialysis machine (or other medical machine comprising a flow meter).

FIG. 2 shows how the fluid flow is shown on the vertical axis, through pump segments of five different brands is heavily dependent on the pressure, as shown on the horizontal axis upstream of the pump at a constant pump speed. Despite a constant pump speed of 21 revolutions per minute, the flow drops rapidly with reduced pressure upstream of the pump. Large negative pressure upstream of the pump can occur, for example, if too narrow a needle is chosen or if the needle and/or blood tubes are blocked in some way between the patient and the pump. One reason for this can be that the negative pressure has a tendency to keep the pump segment pressed together even after the pump roller has passed. This effect is of course reduced if the pump segment has a large wall thickness and an elastic material is used.

FIG. 3 shows how the fluid flow through one and the same pump segment is dependent on time. This figure also shows how the pump efficiency changes with time for five different brands of pump segments.

One way of calibrating a peristaltic pump segment using a fluid flow meter internal of the dialysis machine is shown in FIG. 4. In this first embodiment, the dialyzer 2 is disconnected, compared with FIG. 1, and hoses 5 and 6 are connected to a safety by-pass circuit 9, including a pressure monitor 10. The dialysis machine is adapted so that certain machine operations can only be performed when hoses 5 and 6 are connected to by-pass circuit 9. Such operations are, for example, disinfection and cleaning of the machine, and include calibration of the peristaltic pump according to the first embodiment of the present invention.

By-pass circuit 9 includes a second inlet connection 15, which can be placed on the dialysis machine or be a T-connector at hose 6 or hose 5, as shown in FIG. 4. The connector 15 is connected to the outlet of the peristaltic pump segment.

The inlet of the peristaltic pump segment is connected to the bag or container 40 comprising sterile priming solution, as described in connection with FIG. 1.

Furthermore, the pump segment comprises a connector 16 for connection to a pressure meter positioned internal of the dialysis machine. Thus, the inlet pressure to the peristaltic pump can be measured by the internal pressure meter. The measured pressure is fed to a control and/or monitoring circuit 25, which also includes an inlet for rotor speed of the peristaltic pump.

The dialysis machine is now operated so that a certain dialysate priming flow passes inlet 31, pump 20, fluid flow meter 19, dialysate outlet 32, by-pass circuit 9, return inlet 33, fluid flow meter 18, and pump 21 to waste outlet 34. Pumps 20 and 21 are driven so as to provide a predetermined pressure corresponding to normal outlet pressure for the peristaltic pump during normal operation, for example a positive pressure of about 200 mm Hg.

The peristaltic pump is operated at a certain constant revolution rate, whereby sterile solution is pumped from contain 40, through pump segment 36 to connector 15 and then through fluid flow meter 18 to the waste outlet 34. The dialysis machine measures a fluid flow differential between fluid flow meters 19 and 18, and the differential is the addition from the peristaltic pump. At the same time, the pressure at the inlet of the peristaltic pump segment is measured.

The measured pair of values are stored in the calculating circuit 25, which usually is a computer of the dialysis machine. Then, the inlet pressure is changed and new pairs of measured values of the fluid flow and the inlet pressure are stored. The procedure is repeated until sufficient numbers of pairs of measured values are obtained. The computer calculates a calibration curve, which is then used for determining the actual fluid flow during subsequent operation of the dialysis machine.

The different inlet pressures can be obtained in different ways. Thus, it is possible to alter the height of the container 40, thereby to obtain different inlet pressures as suggested by arrow 24. It is usually desired to have negative pressures, and it is not possible to lower the container 40 too much. In order to have a more convenient adjustment of the inlet pressure, an adjustable throttle valve 23 is used, as shown in FIG. 4. Preferably, the throttle valve is positioned at the medical machine and is controlled by said machine. Alternatively, it is possible to place the throttle valve at the inlet hose 42, whereby the valve can be adjusted manually or automatically.

The method according to the first embodiment can be used in connection with initial filling of the dialysis machine, when no dialyzer is connected.

In a second embodiment shown in FIG. 5, the calibration is performed during priming of the dialyzer, as shown and described in connection with FIG. 1. However, the outlet from the dialyzer 12 is not fed to waste 41, but is connected to an inlet connector 15' of the dialysis machine, adjacent return inlet 33. The connector 15' is shown in FIG. 5 as a T-connector of hose 6.

The operation of the second embodiment is the same as for the first embodiment, but has the advantage that the dialyzer 2 is ready for use after the priming combined with calibration of the peristaltic pump.

It is also possible to use the dialysis solution from the dialysis machine for calibrating the peristaltic pump. A third embodiment of the invention is thus shown in FIG. 6. This embodiment is similar to the embodiment according to FIG. 4, but in this case the inlet to the peristaltic pump is connected to the T-connector 15. The outlet form the peristaltic pump is connected to waste 41.

In this third embodiment, the pumps 20 and 21 of the dialysis machine are driven so as to provide a certain negative pressure in the by-pass circuit 9 where the inlet to the peristaltic pump is connected. The peristaltic pump is started and removes a fluid flow from the dialysate flow. Thus, fluid flow meter 18 shows a lower fluid flow rate than fluid flow meter 19, and the difference is the fluid flow to the peristaltic pump. The pressure between pumps 20 and 21 is equal to the inlet pressure to the peristaltic pump. Thus, the computer of the dialysis machine is provided with pair of values of fluid flow rate and inlet pressures for obtaining a calibration curve.

In this embodiment, it is possible to adjust the inlet pressure continuously from a small positive pressure to a substantial negative pressure for obtaining the entire calibration curve. The calibration procedure can be repeated for several revolution rates for the peristaltic pump rotor to have several sets of calibration curves.

Alternatively, the negative pressure can be obtained with and adjusted by means of an adjustable throttle valve 23 as mentioned above.

FIG. 7 shows a forth embodiment of the invention where the calibration takes place during priming of the dialyzer as in FIG. 5, but using the method of FIG. 6.

It might be impossible to use the dialysate for calibrating the peristaltic pump segment if it cannot be assured that the dialysate is completely sterile, since the pump segment subsequently will be used for passing blood in an extracorporeal circuit, which must be sterile.

However, certain dialysis machines have an outlet for sterile filtered solution used for infusion during hemofiltration or hemodiafiltration, either post- or preinfusion. Such a dialysis machine is, for example, GAMBRO AK100 ULTRA.

According to a fifth embodiment of the present invention, as shown in FIG. 8, the dialysis solution used for priming and calibration is first passed through a sterile filter. The dialysis solution through inlet 31 is passed through pump 20 and fluid flow meter 19 to a sterile filter 45, which can be a hollow fiber filter or any other filter having a membrane capable of passing solutes having a low molecular weight while preventing bacteria and endotoxins form passing through the membrane.

The filtered dialysis solution is emitted through a sterile solution outlet 46 and usually added to an infusion inlet of the drip chamber. A preinfusion is performed by adding the sterile filtered dialysis solution adjacent inlet 11.

The fifth embodiment of the present invention includes using the sterile filtered solution for priming the dialyzer 2 and calibrating the peristaltic pump segment. This fifth embodiment is shown in FIG. 8 and corresponds in all essentials to the fourth embodiment shown in FIG. 7, but in this case the sterile filter 45 has been added. The operation of same is obvious from the above description.

A sixth embodiment of the invention is shown in FIG. 9 and comprises a dialyzer 2' used for hemofiltration, or a so-called hemofilter. Such a hemofilter lacks inlet 7 for dialysis solution, and an ultrafiltrate is taken out from the blood through outlet 8'. The ultrafiltrate is compensated for by addition of substitution solution from sterile filtered outlet 46 as mentioned above. This hemofilter is primed by dialysis solution from sterile filtered outlet 46. According to the sixth embodiment, the outlet 12 from the hemofilter 2' is fed to the inlet of the peristaltic pump. Thus, the difference between flow meters 19 and 18 is the flow through the peristaltic pump. By means of pumps 20, the inlet pressure to the pump segment can be adjusted. Pump 21 controls the transmembrane pressure. Alternatively, the throttle valve 23 can adjust the inlet pressure. Further operation thereof is obvious from the above-given description.

During some types of dialysis, such a single needle dialysis and for infusion of substitution solution during hemofiltration, a second peristaltic pump is used for such purposes. Such second pump can be calibrated in the same way as described above.

It is noted that the peristaltic pump segment is calibrated according to the present invention while using a priming solution comprised in a container 40 or a dialysis solution from the dialysis machine. It is noted that blood usually is much more viscous than such solutions. However, the calibration curve is essentially independent of which fluid is pumped as long as it is non-compressible, since the variation due to different inlet pressures is primarily dependent on the fact that the pump segment is not returned to its circular shape after each pump stroke. Thus, the calibration curve is mainly a property of the material and dimensions of the pump segment proper.

It is noted that the calibration curve will change with time a shown and described with reference to FIG. 3. Such time dependency is believed to be mainly dependent on fatigue in the material. It is also known that the elasticity of most plastic materials is very dependent on the temperature. Thus, it is preferred to perform the calibration at a temperature close to 37 degrees Celsius.

Such a temperature is easily achieved in the embodiments according to FIGS. 6, 7 and 8. In the embodiments according to FIGS. 4 and 5, such temperature can be obtained by heating the priming solution in container 40.

In order to obtain a calibration curve, the calibration pair values are compared to known calibration curves stored in the medical machine, and the most correct calibration curve is selected. To select a correct curve, it is sufficient to have two pairs of values. One of the pair values can be given by the manufacturer for the actual type of pump segment, although measured values are preferred.

Generally, the calibration curve is a second degree curve and it can be approximated by using three different pair values (of which one can be provided by the manufacturer).

It is possible to take several measured pair values for the same input pressure and calculate the mean value thereof for increasing the probability of having the correct calibration curve. Finally, as described in connection with FIG. 6, it is possible to obtain the entire calibration curve or set of calibration curves by continuously adjusting the inlet pressure and measuring the corresponding fluid flow. Further alternatives are obvious to a skilled person.

Account is also taken for the dependency of the fluid flow upon time. Such adjustment is less dependent on different properties of the actual pump segment used, but is more constant for the actual brand of pump segment, and is furthermore rather small, such as less than about 5%. Thus, values obtained from a data sheet can be used for such compensation.

It is evident from FIG. 3 that decrease in fluid flow is obtained after about 60 minutes and for some types even earlier, such as after 30 minutes. By performing the calibration after such time periods when the decrease has substantially occurred, such as after 15, 30 or 60 minutes, such time dependency can be neglected.

The actual fluid flow through the peristaltic pump during operation of the medical machine can be obtained by measuring the inlet pressure and revolution rate of the peristaltic pump. From the calibration curves, an actual fluid flow can be determined. Such actual flow can be shown on the medical machine on a display thereof. Alternatively, said actual flow can be fed to a control device adapted to adjust the peristaltic pump to obtain a desired fluid flow. Further possibilities are obvious to a skilled person.

As mentioned above, the invention is particularly intended to be used during dialysis. Some dialysis machines, such a GAMBRO AK100, have an internal fluid flow meter directly measuring the fluid flow by using a magnetic field and measuring the electric properties of the fluid flow under influence of the magnetic field. Other dialysis machines have other types of fluid flow meters using other physical properties for measuring the fluid flow. Still further dialysis machines have constant displacement pumps for measuring the fluid flow, and simultaneously pumping the fluid, i.e. generating a pressure. All such types of "flow meters" are intended to be within the definition of the present invention.

The invention is, of course, not limited to the embodiments described above, but can be varied within the scope of the appended claims. Different combinations of features and properties from the described embodiments can be used. It should hereby be observed that a dialysis machine ordinarily contains a large number of components apart from those shown schematically in the figures. Additionally, account can also be taken of further operative factors apart from those mentioned above. For example, the height difference between the pressure meter 16 and the safety coupling 9 can also be taken into account.

What is claimed is:

1. A method for calibrating a peristaltic pump including a replaceable tube segment having an inlet and an outlet and propelling means for propelling a fluid through said replaceable tube segment, said method comprising introducing a fluid into said inlet of said replaceable tube segment, pumping said fluid through said replaceable tube segment by operating said propelling means at a substantially constant propelling rate, measuring at least one adjusted inlet pressure for said fluid at said inlet to said replaceable tube segment, and measuring the fluid flow rate through said replaceable tube segment corresponding to said at least one adjusted inlet pressure in order to thereby obtain at least one calibration pair value for said peristaltic pump.

2. The method of claim 1 wherein said peristaltic pump is adapted for use with medical treatment apparatus including an internal fluid flow meter, and wherein said measuring of said fluid flow rate is carried out utilizing said internal fluid flow meter.

3. The method of claim 2 wherein said measuring of said fluid flow rate comprises flowing said fluid from said outlet of said replaceable tube segment to said internal fluid flow meter of said medical treatment apparatus.

4. The method of claim 3 including providing said adjusted inlet pressure by adjustably throttling said fluid flow to said inlet of said replaceable tube segment.

5. The method of claim 2 wherein said medical treatment apparatus includes at least one fluid outlet, and including measuring said fluid flow rate by passing a fluid from said at least one fluid outlet to said inlet of said replaceable tube segment and measuring said fluid flow rate utilizing said internal fluid flow meter of said medical treatment apparatus.

6. The method of claim 5 wherein said medical treatment apparatus includes at least one internal pump, and including supplying said fluid to said inlet of said replaceable tube segment by means of said at least one internal pump.

7. The method of claim 2 wherein said medical treatment apparatus comprises a dialysis machine.

8. The method of claim 1 wherein said measuring of said fluid flow rate comprises measuring at least two of said fluid flow rates through said replaceable tube segment corresponding to at least two of said adjusted inlet pressures in order to obtain at least two calibration pair values for said peristaltic pump, and calculating a calibration curve for said calibration pair values representing the relationship between said fluid flow rate and said inlet pressure at said substantially constant propelling rate.

9. The method of claim 8 including obtaining at least a third calibration pair value for said peristaltic pump comprising a standard pair value corresponding to said peristaltic pump.

10. The method of claim 8 including selecting an actual inlet pressure and an actual constant propelling rate and determining the actual fluid flow rate from said calibration curve for said selected actual inlet pressure and said selected actual constant propelling rate.

11. The method of claim 1 including adjusting said at least one calibration pair value by compensating for the time dependency of said fluid flow rate.

12. The method of claim 11 including compensating for said time dependency by means of a standard value compensation for said peristaltic pump.

13. The method of claim 11 including compensating for said time dependency by permitting a predetermined time period to elapse for said pumping of said fluid through said replaceable tube segment before calibrating said peristaltic pump.

14. The method of claim 13 wherein said predetermined time period comprises at least about 15 minutes.

15. The method of claim 13 wherein said predetermined time period comprises at least about 30 minutes.

16. A medical treatment apparatus including an internal fluid flow meter and a peristaltic pump comprising a replaceable tube segment including an inlet and an outlet and propelling means for propelling a fluid through said replaceable tube segment at a substantially constant propelling rate, said apparatus including peristaltic pulp calibration means comprising a first hose for connecting a source of a solution to said inlet of said replaceable tube segment, a second hose for connecting said outlet of said replaceable tube segment to disposal means, providing means for providing said fluid to said inlet of said replaceable tube segment, pressure measuring means for measuring an adjusted inlet pressure for said fluid at said inlet to said replaceable tube segment, flow measuring means for measuring the fluid flow rate of said fluid through said replacement tube segment during maintenance of said adjusted inlet pressure in order to thereby obtain at least one calibration pair value for said peristaltic pump, and calculation means for calculating a calibration curve from said at least one calibration pair value representing the relationship between said fluid flow rate and said inlet pressure at said substantially constant propelling rate.

17. The apparatus of claim 16 wherein said flow measuring means comprises said internal flow meter.

18. The apparatus of claim 17 including at least one fluid inlet member, and wherein said second hose connects said outlet of said replaceable tube segment to said at least one fluid inlet member upstream of said disposal means, whereby said fluid flow rate can be measured by said internal fluid flow meter.

19. The apparatus of claim 17 including at least one fluid outlet member, and wherein said first hose is connected to said at least one fluid outlet member as said source of said solution, whereby said fluid flow rate can be measured by said internal flow meter.

20. The apparatus of claim 19 including pressure adjusting means for adjusting the pressure at said at least one fluid outlet member thereby adjusting the pressure of said inlet to said adjustable pump segment.

21. The apparatus of claim 16, including determining means for determining the actual fluid flow rate for an actual inlet pressure and an actual constant propelling rate utilizing said calibration curve.

22. The apparatus of claim 16 including an adjustable throttle valve associated with said inlet of said adjustable pump segment for adjusting the inlet pressure of said adjustable pump segment to said adjusted inlet pressure.

23. The apparatus of claim 16 wherein said medical treatment apparatus comprises a dialysis machine.

* * * * *